US012741144B2

(12) United States Patent
Yigit et al.

(10) Patent No.: US 12,741,144 B2
(45) Date of Patent: Sep. 22, 2026

(54) FITTING SYSTEM FOR FULLY IMPLANTABLE MIDDLE EAR IMPLANT

(71) Applicant: ORTA DOGU TEKNIK UNIVERSITESI, Ankara (TR)

(72) Inventors: Halil Andac Yigit, Ankara (TR); Salar Chamanian, Ankara (TR); Onur Ergun, Ankara (TR); Haluk Kulah, Ankara (TR)

(73) Assignee: ORTA DOGU TEKNIK UNIVERSITESI, Ankara (TR)

( * ) Notice: Subject to any disclaimer, the term of this patent is extended or adjusted under 35 U.S.C. 154(b) by 214 days.

(21) Appl. No.: 18/685,929

(22) PCT Filed: Aug. 23, 2021

(86) PCT No.: PCT/TR2021/050851
§ 371 (c)(1),
(2) Date: Feb. 23, 2024

(87) PCT Pub. No.: WO2023/027650
PCT Pub. Date: Mar. 2, 2023

(65) Prior Publication Data

US 2025/0177749 A1 Jun. 5, 2025

(51) Int. Cl.
*A61N 1/36* (2006.01)

(52) U.S. Cl.
CPC ................................ *A61N 1/36039* (2017.08)

(58) Field of Classification Search
CPC ... A61N 1/36039; H04R 25/606; H04R 25/70
See application file for complete search history.

(56) References Cited

U.S. PATENT DOCUMENTS

| | | | | |
|---|---|---|---|---|
| 6,342,035 | B1 * | 1/2002 | Kroll | H04R 25/606 607/57 |
| 6,879,695 | B2 * | 4/2005 | Maltan | H04R 25/606 381/322 |
| 7,043,303 | B1 * | 5/2006 | Overstreet | A61N 1/36039 607/57 |
| 10,219,081 | B2 * | 2/2019 | Wernaers | H04R 25/554 |
| 2005/0261748 | A1 | 11/2005 | van Dijk | |
| 2006/0178711 | A1 * | 8/2006 | Patrick | A61N 1/36039 607/57 |
| 2010/0280307 | A1 * | 11/2010 | Lineaweaver | A61N 1/36038 607/57 |
| 2011/0218592 | A1 * | 9/2011 | Svirsky | A61N 1/36039 607/57 |
| 2013/0129125 | A1 * | 5/2013 | Meskens | H04R 25/606 381/314 |

(Continued)

FOREIGN PATENT DOCUMENTS

| | | | | |
|---|---|---|---|---|
| CN | 109966022 A | | 7/2019 | |
| CN | 112512627 A | * | 3/2021 | A61N 1/0541 |
| EP | 1338301 A1 | | 8/2003 | |

(Continued)

*Primary Examiner* — Carl H Layno
*Assistant Examiner* — Heidi A Hilsmier
(74) *Attorney, Agent, or Firm* — Bayramoglu Law Offices LLC

(57) ABSTRACT

A fitting system for fully implantable middle ear implant uses acoustic waves to tune cochlear implant device according to patient comfort.

11 Claims, 4 Drawing Sheets

(56) References Cited

U.S. PATENT DOCUMENTS

2018/0352351 A1* 12/2018 Yoo ........................ H04R 25/70

FOREIGN PATENT DOCUMENTS

| | | | | | |
|---|---|---|---|---|---|
| EP | 3120898 | A1 * | 1/2017 | ......... | A61N 1/36039 |
| EP | 3244635 | A1 | 11/2017 | | |
| WO | WO-2008048383 | A1 * | 4/2008 | ........... | A61B 5/0051 |
| WO | 2011038231 | A2 | 3/2011 | | |

* cited by examiner

FITTING SYSTEM FOR FULLY IMPLANTABLE MIDDLE EAR IMPLANT

CROSS REFERENCE TO THE RELATED APPLICATION

This application is the national phase entry of International Application No. PCT/TR2021/050851, filed on Aug. 23, 2021, the entire content of which is incorporated herein by reference.

TECHNICAL FIELD

The invention relates a fitting system for fully implantable middle ear implant which uses acoustic waves to tune cochlear implant device according to patient comfort.

BACKGROUND

According to the UK NHI, in 2011, 219,000 people worldwide had cochlear implants (CI). This number has increased by over 300000 per year since 2013. Considering that there were 12000 users in the UK in 2011, there is a potential of 1400000 users with the current world population to consider. In the future, CI's will have smaller, better microphone systems, fully implanted designs, which will not affect the MRI quality. As the functional results and hearing success of the CI's improved, it has become more important to be less noticeable from the outside. This trend will result in completely implanted CI systems that prevent users from being perceived as "disabled". Fully implanted CI systems have not yet been applied commercially, but they are required to solve MRI and calibration problems.

Fully implantable middle ear implants solve innate and subsequent hearing problems. They are similar to cochlear implants which consist of an electrical stimulation circuit, a microphone and a power unit. The stimulation circuit generates a stimulation current to stimulate the neural cells inside the inner ear. The hearing and comfort level of each person may vary. Hence, cochlear implants are designed to be adjusted and calibrated for different patients to increase their quality of life. For this purpose, the active number of channels and their gain level and frequency ranges can be tuned by a fitting system.

EP 1338301 A1 offers an algorithm in which patient fitting correlates with the patient's medical history. By this way, patient fitting calibration is optimized and can be performed with a minor adjustment after CI operation. Another algorithm is offered by WO 2011 038231 A2. In this patient fitting algorithm, the patient data is determined from a database of the CI implant users. These inventions offer elimination of time-consuming manual fitting or additional specialized electronics.

Another patent document U.S. Pat. No. 7,043,303 B1 simplifies the fitting process for CI's and stimulation strategies by adding electronical components. By this component the patient fitting system can be self-programmable, does not require threshold level determination and patient feedback. However, it requires an extra interface unit and cannot be used for fully implantable devices since it is a wired system.

The patent document US 2005 0261748 A1 offers a method for providing better sound to the low residual acoustic hearing capacity area of the cochlea by means of a calibrating system. The low residual acoustic hearing capacity area is determined via electrical stimulation tests and the CI system is calibrated according to these test results. However, this system restricts the number of channels. If the number of channels is low, finding the area with low residual acoustic hearing capacity becomes challenging.

SUMMARY

The present invention is related to a fitting system for fully implantable middle ear implant that meets the requirements mentioned above, eliminates all of the disadvantages and brings about some new advantages.

This invention presents a system for fitting fully implantable middle ear implants by using acoustic waves to tune cochlear implant device according to patient comfort. The device includes transducers and electronics to be fitted to middle ear which can be a part of a cochlear implant or separate devices themselves. The fitting data is modulated on acoustic carrier frequency and transferred through hearing mechanism. Sound transducers, placed in the middle ear, are used to sense generated vibration on the eardrum or ear bones. The electronic device configured to connect to transducer receives the sound wave, extracts the data, and reconfigures the implant device. This device provides a fitting option for fully implantable concept and self-fitting for patients. The transducers are also used for transferring data from an implant to a source device by vibrating middle ear bones and eardrum to generate back-telemetry sound waves. While the acoustic fitting system renders the fully implantable cochlear implant practicable, it also solves the magnetic resonance imaging (MRI) compatibility problem and allows patients to self-fit.

In this invention, acoustic waves are used to transfer data for the benefit of human hearing mechanism for fitting of implants in middle ear. This fitting method eliminates the RF link and solves the MRI problem in ear implants. Any algorithm can be adapted and modulated acoustic wave can easily be propagated with the mobile device or other audio devices. This invention facilitates self-fitting with electronic or mobile devices using apps.

BRIEF DESCRIPTION OF THE DRAWINGS

The figures used to better explain a fitting system for fully implantable middle ear implant developed with this invention and their descriptions are as follows.

DETAILED DESCRIPTION OF THE EMBODIMENTS

The details for a better explanation of the fitting system for fully implantable middle ear implant developed with this invention are provided below.

Middle-ear implants require calibration for different patients. The calibration of an implanted system can be performed with wireless data transfer. Commercial devices use RF Links, magnets and high carrier frequency for data transfer. The data can also be transferred to the implant via ear and low carrier frequency by using a transducer which is mounted into the middle ear. With acoustic band carrier frequency, implants can be calibrated with notebooks and mobile phones by the patient.

Replacing transducer form RF to transducer solves the MRI compatibility problem. Conventional cochlear implants use magnets for alignment. These magnets can cause local heating and irritation or driving force under MRI. Patients with conventional cochlear implants must have a surgery before getting an MRI to remove the magnet lying underneath the skin.

The proposed calibration method can be used with the transducer on the cochlear implant system and in the fitting process there is no need to use an extra transducer. The patient fitting system operate as follows: the patient fitting bits are generated and modulated on the mobile phone. Then, the modulated sound is transferred into the ear with natural ear mechanics. The transducer in the middle ear converts the sound to electrical signals. These electrical signals are converted to the patient fitting bits with the help of the low power electrical circuits.

The removal of the RF coils and magnet from the cochlear implants open up available space in the human body. Extra battery cells can be added to this free space, and life time of the implant can be extended. Since the RF band frequency is higher than the acoustic band, the demodulation module requires a higher clock frequency. A higher frequency, in turn, makes the circuits more complicated and power hungry.

User friendliness: In an RF link, the sound processor should be programmed or the saved data should be used for fitting which constitutes the main problem in such systems. However, in this invention, various data forms can be generated and verified by the system and there is no need for complex algorithms and a technician to calibrate the implant.

Transmitter:

The transmitter module of the system is just an application which can be used with any electronic device with an audio output. Calibration data signal can be generated by an electronic device with a specific carrier frequency. The carrier frequency should be set to a pre-determined calibration channel frequency and the application arranges the bits of the calibration. In order to minimize noise's impact, headphones should be used during the calibration process.

Figure 1:
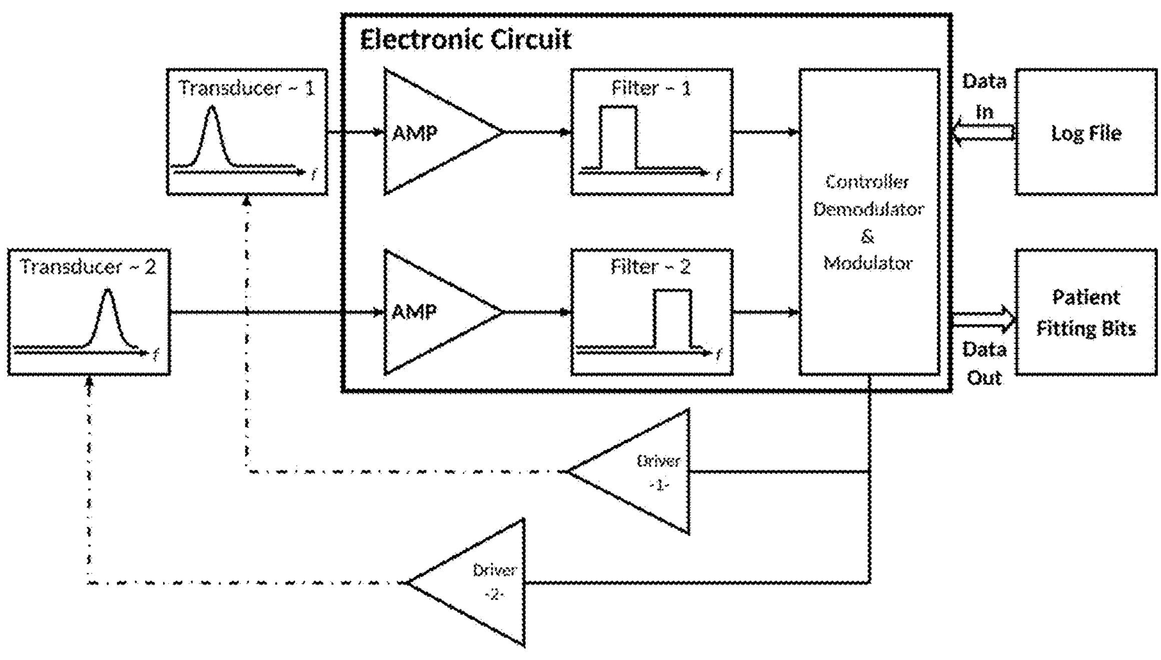
FIG. 1 Block Diagram of the Receiver Module

Receiver:

FIG. 1 shows the two-channel implantation of the receiver module. The receiver can be implanted as single channel or multi-channel according the transfer data and modulation method. The transducers (transducer 1 and transducer 2 as shown in FIG. 1) start to generate voltage from the specific calibration sound. These voltages are amplified with amplifiers (AMP) then filtered with electrical filters (filter 1 and filter 2 as shown in FIG. 1) for eliminating the noise and false inputs. The filter outputs are combined at the controller for decoding and controlling the system for different patients. The controllers also control the drivers (driver 1 and driver 2 as shown in FIG. 1) and generate data for back telemetry. Data-out process is shown in FIG. 1.

Transducer:

The transducers can be a piezoelectric or an electrostatic transducer. Both of them receives the vibration and generates electrical signal at the output. The piezoelectric translation uses charge redistribution and an electrostatic transducer uses capacitance change for electrical output generation. Both have the similar characteristic, however, the rest of the circuits have to be arranged according to the type of the transducer.

The transducer characteristic is important for the calibration system. The transducer frequency response can be flat like a microphone or have a high Q (quality factor) bandpass characteristic. While using flat response transducer, the electrical filter should have high Q because the transducer is more sensitive to noise. While using a bandpass transducer, the frequency of the input signal depends on the structure and input source calibration could be complex. However, both transducers are feasible for the proposed calibration system with small changes. Since low frequencies are used for data transfer, the calibration time may be long. To reduce calibration time, more than one transducer can be used. When the number of transducers is increased, input signal generation becomes more complex.

The patient fitting device in the system where piezoelectric and electrostatic transducers are used for receiving the acoustic waves is MRI-friendly and eliminates the requirement of RF coils and also related magnets.

Front-End Electronic Circuits:

The transducer output voltage is very low since the transducer volume is restricted. The output voltage should be amplified for processing data. The input amplifier should be a low noise amplifier for better detection and low electrical noise. Since data is transferred to the system by air, the output of the transducer will be affected from ambient noise. The filter eliminates the ambient noise by suppressing redundant frequency components. The filter should be bandpass and the filter bandwidth should be small for correct operation.

Modulation Method:

Modulation and encoding are required for wireless data transfer. The modulation choice is affected by the transducer bandwidth and center frequency. The encoding should be implanted for data transfer and it should be different for every patient for safety.

Figure 2:
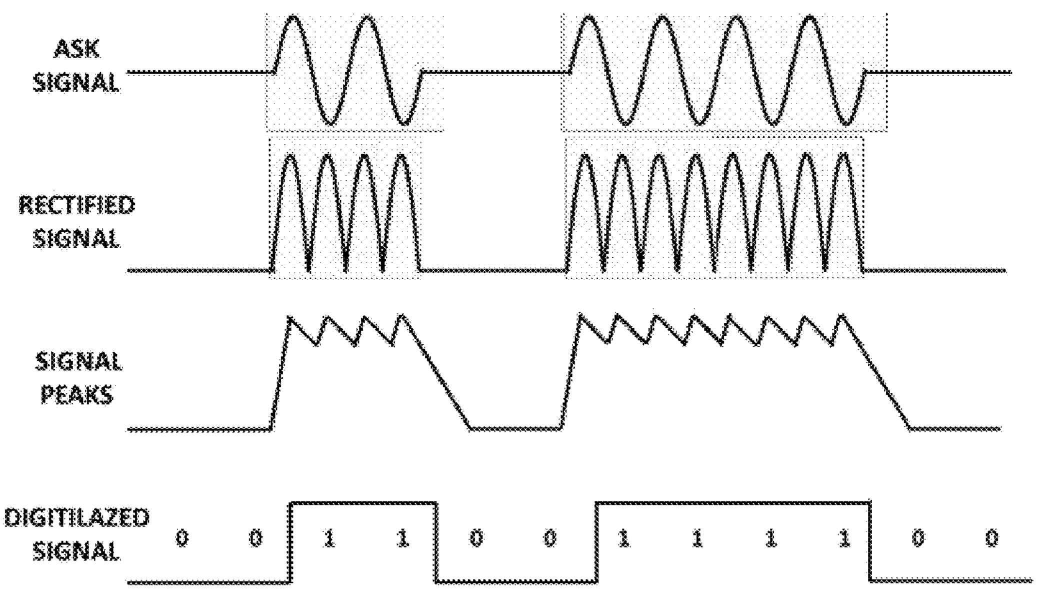
FIG. 2 ASK demodulation steps.
Figure 3:
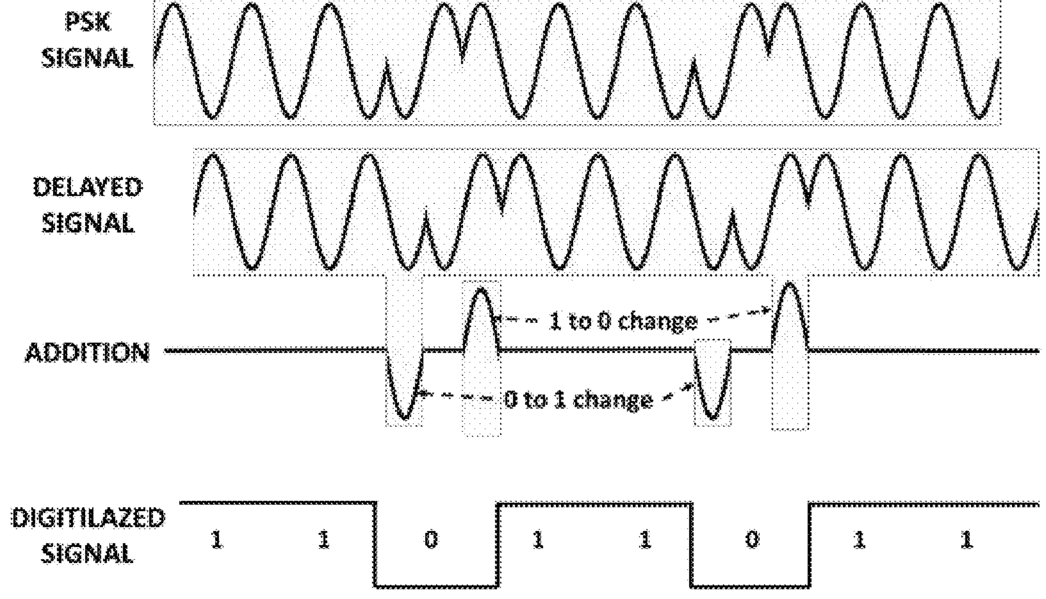
FIG. 3 PSK demodulation steps

FIG. 2 shows the ASK signal, rectified signal, signal peaks and digitilazed signal. Since the transferred data is in digital form, digital modulations are more suitable for the system. Amplitude Shift Keying (ASK), Frequency Shift Keying (FSK) and Phase Shift Keying (PSK) are the most commonly used digital modulation methods. The FSK method requires two different frequencies for modulation and demodulation, so generation and calibration of the frequencies can be challenging. PSK and ASK modulation requires a single frequency and they can both be used for modulation. An ASK demodulation circuit requires a rectifier, a peak detector and a low pass filter. FIG. 3 shows the basic demodulation steps of the ASK modulation, where the modulated signals rectified for peak detection operation after peak detection signal are digitalized by low pass filter. The input signal and delayed input signal are added for PSK demodulation delay circuit and the added circuit will be sufficient for demodulation. The demodulation steps of the PSK can be seen in FIG. 3. The PSK signal, delayed signal, addition, 1 to change 0 and 0 to change 1 process and digitilazed signal are shown in FIG. 3.

Patient fitting time depends on the carrier frequency and the number of bits. For the fast operation, the carrier frequency should be selected as high as possible; however, the characteristic of eardrum limits the range of applicable frequency. The fitting time is directly proportional with the number of transferred channels, the number of bits per channel and the period of the carrier frequency. Moreover, the fitting time can be decreased by adding additional transducers.

In the patient fitting device in the system where both flat and high-Q characteristics of the transducer are adaptable, the signal received by the flat-response transducer is configured to be filtered electrically to achieve prescribed frequency band.

In the patient fitting device where transmitted acoustic waves are preferably modulated with PSK method, other modulation methods including ASK and FSK may be implemented.

Figure 4:
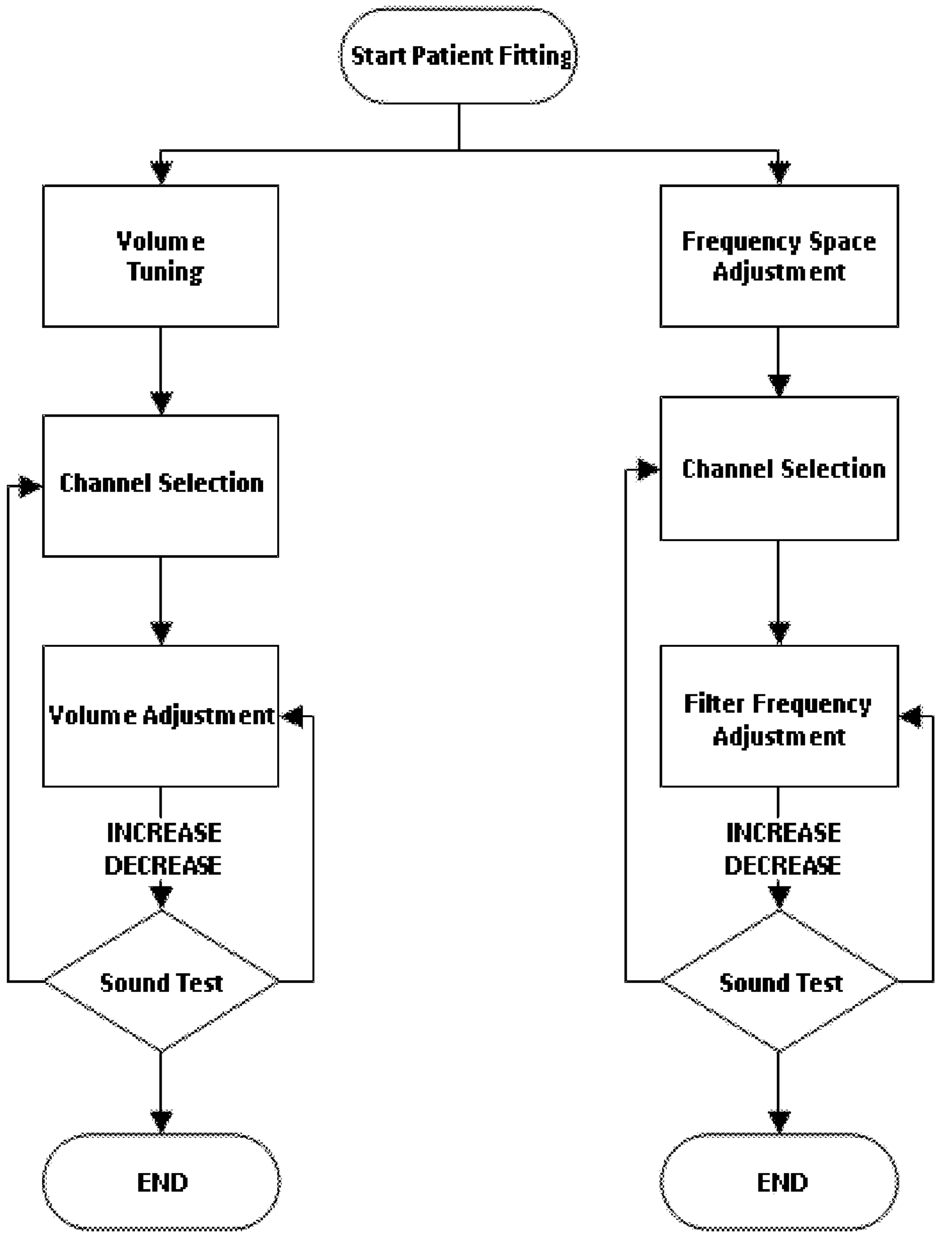
FIG. 4 Operation diagram of the patient fitting system

Operation Chart:

FIG. 4 represents the operation chart of the patient fitting system. In the volume tuning section, the channel volume can be increased or decreased after the adjustment by means of a test sound generated with the system. After the testing, the patient can further increase or decrease the volume in the selected channel or can select another channel if the test sound is not understandable. In the frequency space adjustment following the surgery, the electrode locations and input filters are calibrated. After channel selection, the filter frequency is adjusted and the sound test is performed with a multi-frequency test sound. According the patient response, the filter can be tuned more accurately.

Figure 5:
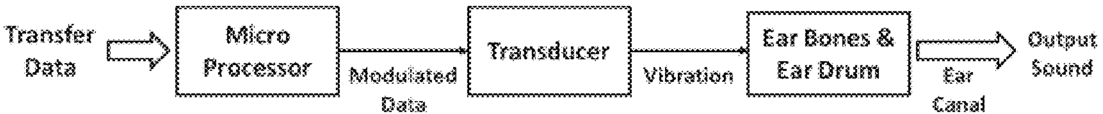
FIG. 5 Block Diagram of the Back Telemetry System.
Figure 6:
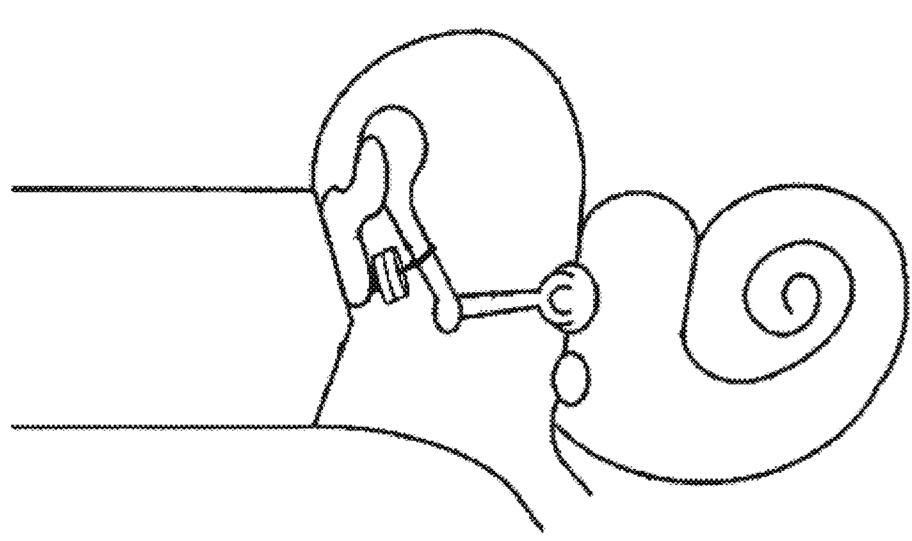
FIG. 6 Back Telemetry Data Acquisition Scheme.

Back Telemetry:

The patient fitting system also offers a back telemetry option by adding a modulator circuit. Back telemetry can be used for data transfer from the implant to a mobile device. The data can be a log file of the implant or battery percentage. The block diagram of back telemetry is given in FIG. 4. After transfer data generation the data is digitalized by a microprocessor. Digital transfer data is modulated and excited by the transducer. The transducer generates vibrations and these vibrations are conducted to the eardrum via ear bones. The eardrum (FIG. 6) translates the vibrations into a sound signal and this signal can be caught by a microphone (FIG. 5), which is placed in the ear canal. The microphone converts the sound signal to an electrical signal and this signal is processed by any electrical device incorporating a specific application.

The fitting system for fully implantable middle ear implant that uses acoustic waves to tune cochlear implant device comprises

- A transmitter module which is an application which can be used with any electronic or mobile device with an audio output,
- A receiver module which is implanted as single channel or multi-channel according to the transfer data and modulation and comprises a patient fitting device,
  - wherein said fitting device comprises;
  - an acoustic wave transmitter to generate a modulated signal for transferring data,
  - an acoustic transducer to sense and convert the sound or acoustic wave into electrical signals,
  - a front-end electronic circuit (an electronic circuit) configured to connect to the transducer to receive, amplify, filter and demodulate the signals including sensing amplifiers filters, and a processor circuit to modulate, demodulate and control the signals,
  - a back-telemetry including a microphone and driving circuits configured to connect to the transducer for actuation and used for data transfer from the implant to a mobile device.

Other aspects of the invention are as follows:

- The patient fitting device tunes volume and performs frequency shift of middle ear implants with acoustic-band carrier frequency.
- The patient fitting device generates bits connected to drivers for actuating the transducers at their resonance frequencies.
- The microphone in back telemetry is placed in the ear canal to receive the waves transferred through bones and eardrum by the transducer.
- The transducer is placed anywhere in the middle ear to transfer the vibration or associated with the cochlear implant transducer.
- The transducer is either a piezoelectric transducer that uses charge redistribution or an electrostatic transducer that uses capacitance change for electrical output generation and receiving the acoustic waves.
- The fitting device transmits acoustic waves which are modulated with amplitude shift keying, frequency shift keying or phase shift keying method.
- The system comprises a fitting device which is provided to convey modulated waves through the natural hearing mechanism including the eardrum and middle ear bones.
- The electronic or mobile device is a device which is capable of running apps.
- The transducers are adaptable transducers with both flat and high-quality factor (Q) characteristics.
- The transferring data is transmitted through either one channel or multiple channels corresponding to the number of available transducers.
- An operation method of a fitting system comprising;
- During volume tuning;
- Channel selection,
- Adjusting the channel volume by increasing or decreasing,
- Performing a sound test,
- After the testing, if the test sound is not understandable, increasing or decreasing the volume of the selected channel or the patient selecting another channel,
- During frequency space adjustment;
- After calibration of the electrode locations and input filters following the surgery, adjusting frequency space,
- Channel selection,
- After the channel selection, adjustment of filter frequency by increasing or decreasing, Testing of sound by performing multi frequency sound test.

The invention claimed is:

1. A fitting system for fully implantable middle ear implant that uses acoustic waves to tune cochlear implant device, comprising:

- a transmitter module which is an application on an electronic or mobile device with an audio output, and
- a receiver module which is implanted as single channel or multi-channel according to transfer data and modulation and comprises a patient fitting device,
- wherein the fitting device comprises:
  - an acoustic wave transmitter to generate a modulated signal for transferring data,
  - an acoustic transducer to sense and convert the wave into electrical signals, wherein the transducer is an adaptable transducer with both flat and high-quality factor characteristics,
  - a front-end electronic circuit configured to connect to the transducer to receive, amplify, filter, and demodulate the signals including sensing amplifiers filters,
- a processor circuit to modulate, demodulate, and control the signals, and
  - a back-telemetry including a microphone and driving circuits configured to connect to the transducer for actuation and used for data transfer from the implant to a mobile device.

2. The fitting system according to claim 1, wherein the patient fitting device tunes volume and performs frequency shift of middle ear implants with acoustic-band carrier frequency.

3. The fitting system according to claim 1, wherein the patient fitting device generates bits and is connected to drivers for actuating the transducer at the transducer's resonance frequencies.

4. The fitting system according to claim 1, wherein the microphone in back telemetry is placed in an ear canal to receive the waves transferred through bones and eardrums by the transducer.

5. The fitting system according to claim 1, wherein transducer is placed in a middle ear to transfer vibration.

6. The fitting system according to claim 1, wherein transducer is either a piezoelectric transducer that uses charge redistribution or an electrostatic transducer that uses capacitance change for electrical output generation and receiving the acoustic waves.

7. The fitting system according to claim 1, wherein the fitting device transmits acoustic waves which are modulated with amplitude shift keying, frequency shift keying, or phase shift keying method.

8. The fitting system according to claim 1, wherein the system comprises a fitting device provided to convey modulated waves through a natural hearing mechanism including an eardrum and middle ear bones.

9. The fitting system according to claim 1, wherein transferring data is transmitted through either one channel or multiple channels corresponding to a number of transducers.

10. The fitting system according to claim 1 wherein sensed and converted wave is sound or acoustic wave.

11. An operation method of the fitting system according to claim 1, comprising the following steps during volume tuning:

performing channel selection, adjusting a channel volume by increasing or decreasing, performing a sound test, and after testing, if the test sound is not understandable, increasing or decreasing the volume of the selected channel or a patient selecting another channel, the operation method further comprising the following steps during frequency space adjustment:

after calibration of electrode locations and input filters following surgery, adjusting frequency space, performing channel selection, after the channel selection, adjusting filter frequency by increasing or decreasing, and testing of sound by performing multi frequency sound test.

* * * * *